United States Patent [19]

Linsky et al.

[11] Patent Number: 4,840,626

[45] Date of Patent: Jun. 20, 1989

[54] HEPARIN-CONTAINING ADHESION PREVENTION BARRIER AND PROCESS

[75] Inventors: Cary Linsky, East Brunswick; Timothy Cunningham, Flemington; Eli Pines, Watchung, all of N.J.

[73] Assignee: Johnson & Johnson Patient Care, Inc., New Brunswick, N.J.

[21] Appl. No.: 912,450

[22] Filed: Sep. 29, 1986

[51] Int. Cl.$^4$ ............................................ A01F 13/16
[52] U.S. Cl. .................................... 604/364; 514/56; 600/37; 604/374; 604/286; 128/325
[58] Field of Search ................ 604/364, 11, 286, 288, 604/374; 514/56; 128/156, 334 R, 325, DIG. 22; 600/37

[56] References Cited

U.S. PATENT DOCUMENTS

| | | | |
|---|---|---|---|
| 3,122,479 | 2/1964 | Smith | 128/325 |
| 3,902,497 | 9/1975 | Casey | 128/325 |
| 4,603,695 | 8/1986 | Akada et al. | 604/364 |
| 4,704,131 | 11/1987 | Noishiki et al. | 623/66 |
| 4,745,098 | 5/1988 | Michaeli | 514/56 |

FOREIGN PATENT DOCUMENTS 0213563  3/1987  European Pat. Off. ............. 604/11

OTHER PUBLICATIONS

Milos Chvapil, Modified Collagen Products Preventing Postoperation Concrescence, 1/71 Chemical Abstracts 76(22:131527u.
Philip Geve, Websters Third New International Dictionary, 1965.

Primary Examiner—C. Fred Rosenbaum
Assistant Examiner—Mark O. Polutta
Attorney, Agent, or Firm—Joseph J. Brindisi

[57] ABSTRACT

An improved adhesion-preventative barrier fabric comprising an oxidized regenerated cellulose (ORC) fabric (or matrix having equivalent properties) which is drapable, conformable, adherent to body organs, and substantially absorbable within thirty (30) days in the body, which fabric has heparin absorbed thereon, said heparin being present in a non-toxic, adhesion-preventative, effective amount and potency; and, the process of using said improved barrier fabric or matrix to administer heparin to prevent surgical adhesions.

18 Claims, No Drawings

HEPARIN-CONTAINING ADHESION PREVENTION BARRIER AND PROCESS

FIELD OF THE INVENTION

This invention relates to adhesion barrier materials useful in surgery for preventing post operative adhesions; and is more particularly concerned with a matrix which is drapable, conformable, adherent to body organs, substantially absorbable within thirty (30) days in the body, said matrix having an adhesion-preventative amount of heparin incorporated therein, and is still more particularly concerned, as a preferred version, with an absorbable matrix, such as a fabric of oxidized regenerated cellulose (ORC) which is impregnated with an adhesion-preventative amount and potency of heparin, and to the process of administering heparin topically to an internal body organ by absorbing it on an ORC fabric which is applied to the body organ during surgery.

BACKGROUND OF INVENTION

Post operative adhesions represent a major problem in patients recovering from surgery. When organs and tissues are subject to surgical and related trauma, there is a tendency for adhesions to form between the affected areas and neighboring tissue.

In the case of intestinal surgery, the incidence of adhesions causing intestinal obstructions has been reported as approximately four times that due to strangulated hernia. The post operative formation or reformation of pelvic adhesions is reported to be a major factor contributing to the relatively poor results obtained in infertility surgery.

Various methods have been suggested for reducing the incidence of peritoneal adhesions following surgical intervention, but results have not been entirely favorable. One method involves the application of chemical treating agents to the site of the surgical incision or abrasion in an effort to inhibit the physiological response responsible for the formation of the fibrous tissue which comprises the adhesion mass. In this category are enzymes such as fibrinolysin and papase, polyphloretin-phosphate, oxyphenbutazone, a mixture of phenylbutazone and prednisolone, polyvinylpyrrolidone and dextran.

A second approach to preventing the formation of adhesions is to install a physical barrier material between the site of the surgical activity and the neighboring tissue where adhesions are most expected to occur. In this category are silicone sheets such as Silastic*, a medical grade silicone elastomer available from Dow Corning, Gelfilm*, an absorbable gelatin film available from Upjohn, and Surgicel*, a knit fabric of oxidized regenerated cellulose (ORC) available from Johnson & Johnson Products, Inc.

The results obtained with the prior art materials and methods have varied according to different investigators. In the case of oxidized cellulose, for example, very good results were reported by Larssen, Acta Chir Scand 144: pp. 375–378 (1978) and Raftery, Br. J. Surg. Vol. 67 pp. 57–58 (1980); negative results were obtained by Schroder, Acta Chir Scand 148 pp. 595–596 (1982), Yemini, Int. J. Fertil 29 pp. 194–196 (1984) and Soules, Am. J. Obstet & Gyn, Vol. 143 pp. 829–834 (1982); and mixed results were obtained by Nishimura, Jpn. J. Surg. vol. 13 pp. 159–163 (1983).

In the copending U.S. patent application of Linsky and Cunningham, Ser. No. 768,280, filed Aug. 22, 1985, entitled "Method and Material for Prevention of Surgical Adhesions", the teachings of which are specifically incorporated herein by reference, a particular fabric construction was disclosed resulting in an improved adhesion barrier fabric. That material was a fabric of oxidized regenerated cellulose (ORC) characterized by having a porosity as defined by open area of 12 to 20 percent and a density of from about 8 to 15 mg/cm$^2$. A typical fabric is prepared from 60 denier, 18 filament bright rayon yarn knitted on a 32 gauge 2 bar warp knitting machine. The knit fabric is oxidized using conventional procedures as described for example in U.S. Pat. No. 3,364,200.

ORC fabrics constructed in accordance with the invention of the aforesaid copending patent application have demonstrated superior performance in reducing the incidence of postoperative adhesion formation when compared to fabrics of ORC previously available.

The above fabric was effective in reducing the incidence of postoperative adhesions when positioned as a physical barrier between the site of the surgical activity and neighboring tissue, but further improvement is still possible. Test results using a preferred version of the above fabric, called TC-7, in adhesion reduction in a rabbit uterine horn model, established its ease of handling. It proved simple to apply, conformed well to the structure, adhered in place, and substantially absorbed within two weeks after surgery.

SUMMARY OF THE INVENTION

We have now found unexpectedly that even greater improved results in reducing postoperative adhesions are obtained when a drapable, conformable adhesion barrier fabric constructed of a bioresorbable material, such as the ORC knitted fabric disclosed in the aforesaid copending U.S. patent application Ser. No. 768,280 (hereinafter called TC-7), or other matrix having similar properties, is impregnated with heparin. We have further found that such improved results occur when heparin is used to impregnate even the less effective conventional ORC barrier fabrics, such as Surgicel* brand ORC barrier fabrics (hereinafter "Surgicel". This is especially surprising since heparin alone, e.g., in lavage solution, is not effective to prevent adhesions. Heparin acts as an adhesion-preventing medicament when it is incorporated into the matrix of the present invention. A preferred embodiment of the matrix is ORC fabric. The heparin may be added to the matrix, e.g. ORC fabric, either before or during the surgery.

One advantage of adding the heparin to the barrier fabric is that the fabric absorbs and hods small quantities of heparin, so no excess amount of heparin is used which the body would have to absorb or eliminate. This allows much smaller amounts to be used, and is important when dealing with a potentially toxic substance. It ensures minimal heparin is spilled into or onto other organs or body cavities. By using the matrix or barrier fabric to deliver the heparin to the specific place in the body where the heparin is needed and especially intraperitoneally, the following important benefits are realized: localized delivery, smaller doses, maximum efficacy, minimum side effect, and reduction of lag time to build drug concentration.

The present invention includes both product and related process aspect. In its product aspect, it involves: A matrix (as defined below) having an adhesion-preventative amount and potency of heparin incorporated therein; and also, an improved adhesion-preventative barrier fabric comprising an oxidized regenerated cellulose fabric which is drapable, conformable, adherent to body organs, and substantially absorbable within thirty (30) days in the body, which fabric has heparin absorbed thereon, said heparin being present in a nontoxic, adhesion-preventative, effective amount and potency. Other matrices which could be used should have properties equivalent to the oxidized regenerated cellulose fabric. Among these are included, for illustrative and not exclusionary purposes, materials such as hyaluronic acid, cross-linked and uncross-linked collagen webs, synthetic resorbable polymers, gelatin films, absorbable gel films, oxidized cellulose fabrics and the like, when fabricated into a form which is drapable, conformable, adherent to body organs, substantially absorbable within thirty (30) days in the body, capable of absorbing heparin, and safe for use in surgery.

In its process aspects, the present invention involves: The process of preventing surgical adhesions which comprises positioning as a physical barrier, between the site of the surgical activity and neighboring tissue, a heparin-containing matrix, (as defined above) preferably in the form of an oxidized regenerated cellulose adhesion-preventative barrier fabric; and the process of administering heparin topically to an internal body organ during surgery for the purpose of preventing surgical adhesions which comprises: applying an oxidized regenerated cellulose fabric (or other matrix as defined above) containing heparin absorbed on it to the outer surface of an internal body organ, said fabric (or other matrix) being drapable, conformable, adherent to body organs, and substantially absorbable within thirty (30) days in the body. It also involves the process of delivering heparin topically to a particular organ in the body by absorbing that drug on an ORC barrier fabric or similar type of absorbable matrix, which is then applied to the outer surface of said organ.

OTHER PRIOR ART

Heparin is normally administered intravenously or subcutaneously, not topically.

In an article entitled "Heparin Releasing Antiadhesive Membranes" by Y. Noishiki and T. Miyata published in Jinko Zoki, 14(2), p. 788–791 (1985), a collagen membrane (special treated human amnion) having protamine cross-linked into the collagen network was immersed in 1% heparin solution so the heparin was ionically bound to the protamine which had been cross-linked in the collagen. The resultant heparinized collagen membrane was stitched into place covering a wound on the serosal membrane of the large intestines of dogs. The animals were examined after 3 days, 60 days, 173 days and 687 days. No signs of adhesions were found. The collagen membrane was not biodegradable, since much of it remained even after 687 days. The heparin was released slowly and steadily, so that 76% of the heparin originally present in the membrane was released over a period of three months.

Applicants' invention differs from the above article in using a biodegradable matrix or fabric as a carrier for heparin, the ORC fabric or other matrix being macroscopically broken down within thirty (30) days, (in he case of TC-7, most of it within 4 days); differs in not affixing the carrier matrix or ORC fabric with sutures, but rather in using a pliable, conformable matrix or fabric which remains in place without need for sutures; differs in not exerting a systemic effect but only a local effect provided by the heparin soaked matrix or fabric of the present invention wherein all the heparin is released during the first week rather than slowly and steadily over many months; and differs in that the heparin is not ionically bound to the carrier, but is only absorbed on the matrix or fabric.

DETAILED DESCRIPTION OF THE INVENTION

The matrix useful in the present invention maybe an ORC fabric or be made of any non-ORC material having the characteristics described in connection with the ORC fabric below. Various useful matrices have been mentioned above, and others will be apparent to persons skilled in the art. The preferred matrix useful in the present invention is an oxidized regenerated cellulose (ORC) fabric which is drapable, conformable, adherent to body organs, and substantially absorbable within thirty (30) days in the body. The term "substantially absorbable within 30 days", means that macroscopically by gross observation there is no residual material remaining when the area of the body where the barrier fabric was placed is inspected at the time specified. Such a fabric is easy to apply and will stay in place on the organ without the use of sutures. It is biocompatible and resorbable.

The ORC fabric preferably is knit but could be fabricated in other forms, e.g., nonwoven, or woven, if desired. Commercially available forms of ORC fabric include the following: Surgicel* and Surgicel Nu-Knit* band Adsorbable Hemostat which are described in the PDR (Physicians' Desk Reference), 1986 edition. The TC-7fabric previously identified above is also knitted. It is currently being clinically tested.

For convenience, the description of the present invention will mainly refer to the most preferred embodiment, it being understood that the other matrix materials, which are regarded as less preferred embodiments, would be used in a similar manner.

Heparin (which term is intended to include salt forms, such as the calcium or sodium salt) is commercially available in different potencies, referred to as USP Heparin Units. The heparin potencies tested in the present invention range from 100 to 10,000 USP Heparin Units. We have found potencies of 100 to 2,000 units per six (6) square inches of fabric to be useful, with 500 to 1,500 being preferred. The TC-7 fabric soaked in a solution of 100 Heparin Units was better at preventing adhesions than the TC-7 fabric alone, but the use of 500 USP Heparin Units or more is preferred with the fabric. No statistical difference was seen between TC-7 with 500 Heparin Units or 1000 USP Heparin Units. But 10,000 USP Heparin Units was too potent, since it's use on TC-7 fabric resulted in systemic toxicity in the test animals.

Heparin is preferably used in the same liquid form as would be used for administration by injection, e.g., as Heparin Sodium Injection. Use in this form easily provides the desired number of USP Heparin Units in sufficient liquid to be absorbed on the fabric. Typically 1 ml of Heparin Sodium Injection will wet and saturate or almost saturate a 2"×3" piece of OCR fabric without running off or being visible in the knitted fabric interstices.

The heparin which is absorbed on the ORC (or other matrix material) may be applied to the fabric in liquid form at the time of actual use on a body organ during surgery, i.e., the fabric is cut to the desired size and draped on and conformed to the body organ, and heparin is then applied, in a non-toxic, adhesion-preventative amount and potency, via syringe or pipette or the like to said fabric. The amount of heparin utilized normally should be sufficient to saturate the fabric but not so great that any heparin drips off or is spilled into or onto other organs or body cavities.

The heparin may alternatively be absorbed on the ORC fabric (or other matrix materials) and then dried. The dried heparin-impregnated fabric may then be applied to the body organ during surgery. Moisture from the body organ, or a solution (e.g. Ringer's, saline or water) can be applied to quickly rehydrate and return the heparin to a liquid form. Using this alternative, the ORC fabric with heparin absorbed on it, would be dried in any desired manner, e.g., air-dried, freeze-dried, oven-dried, vacuum-dried etc., after which it would be sealed in any desired type of sealable pouch or container customarily used to contain sterile surgical products such as dressings, sutures, etc., and then sterilized. Mylar foil laminates may be used as the pouch material and radiation sterilization may be used to carry out this alternative. The heparin-impregnated barrier fabric (or matrix) can thus be made easily available for use in surgery in a variety of sizes.

TEST PROCEDURES USED

The efficacy of various heparin-impregnated barrier fabrics of the present invention, as compared to otherwise identical non-heparin impregnated fabrics, was determined by the uterine horn scrape procedure as follows:

New Zealand Female White rabbits weighing between 2.0 and 3.5 kg are utilized. All animals are acclimated in the vivarium for at least two weeks prior to use. Rabbits are individually housed in stainless steel cages. They are fed Purina* Lab rabbit chow (Ralston Purina Co., St. Louis) and given water ad libitum.

Animals are fasted overnight prior to surgery. Anesthesia is induced by an intramuscular injection of 1 ml of a Ketamine (Ketaset*)/Xylazine (Rompun*) solution [1 ml xylazine (20 mg/ml), 2 ml Ketamine (100 mg/ml) and 1 ml sterile water]. Additional anesthesia is administered via the marginal ear vein to maintain the animal on a surgical plane.

All animal surgery is done under aseptic conditions; this includes an iodine scrub, draping, and use of sterile technique. Laparotomy is made through a lower midline incision and the uterine horns are exposed.

Five cm lengths of uterine horn starting 1 cm from the bifurcation are scraped using a #10 scalpel blade. The scrape, controlled in nature, fully removes the serosa and is characterized by engorgement of blood vessels and a small amount of punctate bleeding. Normally 20 strokes with the scalpel are sufficient to induce the described injury. In this model, hemostasis is achieved, when necessary, by tamponade.

The animals are treated by covering each horn with enough fabric so as to completely cover the injured area, i.e., the fabric is cut to a piece 2 inches by 3 inches in size. The appropriate dosage of heparin is then applied to the area by syringing and moistening the fabric with one ml of a heparin solution. The control animals have their horns left untreated, i.e., no fabric or heparin is used.

The musculo-peritoneal layer is closed with 4-0 Vicryl suture (Ethicon, Somerville, NJ), the cutaneous layer with skin staples. Animals are then evaluated for adhesions two weeks after surgery. The evaluation is done via scoring which considers both the extent and severity of the adhesions.

The scoring system relies on the fact that an extensive length of uterine horn is traumatized; thus extent of adhesions can be quantified by measuring the length of the horn to give the following grading:

0=No adhesions
1=25% of traumatized area
2=50% of traumatized area
3=Total involvement Fractional scores are given for extent of adhesions intermediate between the above grades. The severity (tenacity) of the adhesions are measured as follows:

0=No resistance to separation
0.5=Some resistance (moderate force required)
1=Sharp dissection needed The total grade thus is additive giving a range of adhesion scores of 0–4 which represents both extent and severity.

In the following examples, all the adhesion results listed were obtained by the above procedure, or by the above procedure without any heparin.

EXAMPLE 1: TC-7, WITH HEPARIN IN DRIED FORM

TC 7 fabric in 3×4 inch pieces was impregnated with Heparin Sodium Injection, USP. The heparin used was from Elkins Sinn (lot 065096-Exp. date 6/88) in a 10 ml vial at a concentration of 1000 USP units/ml. This solution was diluted 1:1 with sterile water for injection to give a concentration of 500 units/ml.

Two mls of the solution were pipetted on a 3×4 inch piece of fabric (TC 7) which sat in an XT polymer tray. These two mls completely saturated the fabric thus assuring uniform distribution. The wetted fabric was then allowed to sit overnight, during which time the solution flashed off leaving a dry, heparin impregnated fabric.

The dried heparin impregnated TC 7 fabric was then taken out of the tray and placed inside a Tyvek envelope (Grade 1013-B). This was in turn placed inside a foil laminate envelope (Maraflex −0.5 gauge Mylar, 0.00135 foil) which was itself sealed. The packages were then sterilized via use of 2.5 Mrads Cobalt irradiation.

These dried impregnated fabrics were then tested in the rabbit uterine horn model. Each 3×4 inch piece was cut in half into two 2×3 inch pieces; each piece was then applied to a scraped uterine horn of the rabbit. Therefore, each uterine horn was actually treated with 500 units of heparin. After applying each fabric so it was draped over and conformed to the uterine horn, the fabric was wetted with a small amount of saline to enhance its tack to the uterine horn tissue. When the rabbit was sacrificed and the adhesions were evaluated two weeks later, the results were:

| Untreated Controls | Heparin Impregnated Fabric |
|---|---|
| Right 4 | 2 |
| Left 4 | 3 |
| Right 4 | 0 |
| Left 4 | 0 |
| Right 4 | 0.5 |
| Left 4 | 0 |
| | 0 |
| | 0 |
| | 1 |

-continued

| Untreated Controls | Heparin Impregnated Fabric |
|---|---|
|  | 1.5 |
|  | 0 |
|  | 6 |
| X̄ = 4 | X̄ = 0.67 |
| 3 animals | 6 animals |
| 6 horns | 12 horns |

As can be seen, the untreated controls all have severe adhesions while most of the animals with the above heparin-impregnated TC-7 fabric had no adhesions, and a small proportion had moderate adhesions.

EXAMPLES 2–4: TC-7, WITH HEPARIN ADDED IN SITU

In Examples 2–4, the procedure of Example 1 was changed, so the heparin was added directly to the TC-7 fabric. In these Examples, the TC-7 fabric (cut in a 2"×3" size piece) was draped over and conformed to the uterine horn. Then one milliliter (1 ml) of the appropriate concentration of heparin was pipetted onto the TC-7 fabric in situ, which saturated the fabric and made it adhere to the uterine horn. The concentration of heparin used was 1000 USP units/ml starting concentration (1000 USP units actually applied to each uterine horn) for Example 2; 500 USP units/ml starting concentration (500 units actually applied) for Example 3; and 100 USP units/ml starting concentration (100 units actually applied) for Example 4.

The results obtained are shown in the following table:

| | | Example Nos. | |
|---|---|---|---|
| | 2 | 3 | 4 |
| Untreated | Heparin + TC 7 | Heparin + TC 7 | Heparin + TC 7 |
| Control | 1000 Units | 500 Units | 100 Units |
| 4 | 0 | 0 | 0 | 1 | 1.5 |
| 4 | 0 | 0 | 0 | 0.6 | 0 |
| 4 | 0 | 4 | 0 | 0 | 0.75 |
| 4 | 0 | 4 | 0 | 0.6 | 0 |
| 4 | 0 | 0 | 2 | 0 | 2.5 |
| 4 | 0 | 0 | 0 | 0 | 0.5 |
| 4 | 0 | 0 | 0 | 1 | 0 |
| 4 | 0 | 0 | 0 | 0.2 | 0 |
| 4 | 1 | 1 | 1 | 3.5 | 0.5 |
| 4 | 1 | 0.5 | 0 | 2.5 | 0 |
| 3.5 | 0 | 0 | 0 | | |
| 2.5 | 1 | 0 | 1.5 | | |
| 3 | | 0 | | | |
| 2 | | 0 | | | |
| — | — | — | — | | |
| X̄ = 3.64 | X̄ = .48 | X̄ = .38 | X̄ = .76 | | |
| 7 animals | 13 animals | 6 animals | 10 animals | | |
| 14 horns | 26 horns | 12 horns | 20 horns | | |

Using the test results obtained in the various examples, and also in other studies, the effect of varying the potency of heparin (USP units of Heparin units) used to impregnate the TC 7 fabric may be generally summarized, for purposes of comparison, as:

| Control | 3.3 |
|---|---|
| TC 7 alone | 1.8 |
| TC 7 + 100 Units Heparin | 0.8 |
| TC 7 + 500 Units Heparin | 0.4 |
| TC 7 + 1000 Units Heparin | 0.4 |
| TC 7 + 10,000 Units Heparin | Toxic |

EXAMPLE 5: SURGICEL, WITH HEPARIN ADDED IN SITU

Following the procedure of Example 2, but using Surgicel fabric in place of the TC-7 fabric, i.e. a 2 inch by 3 inch piece of Surgicel fabric was draped on each uterine horn, (and where Heparin was added, one ml. was applied in a 1000 USP Heparin units/ml concentration). The Surgicel with heparin was compared to Surgicel used alone without heparin, and also to an untreated control uterine horn. The adhesion results (when the adhesions were evaluated two weeks later) are shown in the following table.

| Heparin & Surgicel 1000 Units | Untreated Control | Surgicel Alone Control |
|---|---|---|
| 1 | 4 | 3.0 |
| 0 | 4 | 3.0 |
| 0 | 4 | 4.0 |
| 0 | 4 | 4.0 |
| 0 | | 4.0 |
| 0 | | 4.0 |
| 1.5 | | 3.0 |
| 0 | | 3.0 |
| .25 | | 2.0 |
| 0 | | 1.5 |
| | | 2.5 |
| | | 3.0 |
| — | — | — |
| X̄ = .28 | X̄ = 4 | X̄ = 3.1 |
| 5 Animals | 2 Animals | 6 Animals |
| 10 Horns | 4 Horns | 12 Horns |

What is claimed is:

1. An improved adhesion-preventative barrier fabric comprising an oxidized regenerated cellulose fabric which is drapable, conformable, adherent to body organs, and substantially absorbable within thirty (30) days in the body, which fabric has heparin absorbed thereon, said heparin being present in a non-toxic, adhesion-preventative effective amount and potency.

2. The product of claim 1 wherein the heparin absorbed on the fabric is applied to the fabric in liquid form at the time of actual use on a body organ during surgery.

3. The product of claim 1 wherein the heparin is absorbed on said fabric and subsequently dried.

4. The product of claim 1 wherein the heparin is absorbed on the fabric, and the heparin-containing fabric is then dried and sealed in sterile form.

5. The product of claim 1 wherein the amount of heparin utilized is sufficient to saturate the fabric but not so great that any heparin drips off.

6. The produce of claim 1 wherein the heparin utilized is in the form of Heparin Sodium Injectable having a potency of 100–2000 USP Heparin Units.

7. The product of claim 1 wherein the oxidized regenerated cellulose fabric is a knit fabric.

8. The process of preventing surgical adhesions which comprises positioning as a physical barrier, between the site of the surgical activity and neighboring tissue, the heparin-containing oxidized regenerated cellulose adhesion preventative barrier fabric of any of claims 1–7.

9. The process of administering heparin topically to an internal body organ during surgery for the purpose of preventing surgical adhesions which comprises: applying an oxidized regenerated cellulose fabric containing heparin absorbed on it to the outer surface of an internal body organ, said fabric being drapable, conformable, adherent to body organs, and substantially absorbable within thirty (30) days in the body.

10. The process of claim 9 wherein the heparin is absorbed on the oxidized regenerated cellulose fabric after the fabric has been applied to said body organ.

11. The process of claim 9 wherein the heparin is absorbed on the oxidized regenerated cellulose fabric before the fabric is applied to the body organ.

12. The process of claims 9, 10 or 11 wherein the amount of heparin on the oxidized regenerated cellulose fabric is such that all the heparin remains on or in the fabric so no excess amount of heparin is present which could be spilled into or onto other organs or body cavities and is sufficient to contribute to improving the prevention of adhesions beyond that which would occur without the heparin but is not more than the amount which saturates the fabric and the potency of the heparin is 100–2000 USP Heparin Units.

13. An improved adhesion-preventative barrier material comprising a matrix which is safe for use in surgery and is drapable, conformable, adherent to body organs, and substantially absorbable within thirty (30) days in the body, which matrix has heparin absorbed thereon, said heparin being present in a non-toxic, adhesion-preventative effective amount and potency.

14. The process of preventing surgical adhesions which comprises positioning as a physical barrier, between the site of the surgical activity and neighboring tissue, the heparin-containing adhesion-preventative barrier material of claim 13.

15. The product of claim 1 wherein the heparin is simply absorbed and not ionically bound to the barrier fabric.

16. The product of claim 1 wherein the oxidized regenerated cellulose fabric is selected from the group consisting of hyaluronic acid, synthetic resorbable polymers, gelatin films, absorbable gel films, and oxidized cellulose fabrics.

17. The process of preventing surgical adhesions which comprises positioning as a physical barrier, between the site of the surgical activity and neighboring tissue, the heparin containing adhesion-preventive barrier material of claim 15.

18. The process of preventing surgical adhesions which comprises positioning as a physical barrier, between the site of the surgical activity and neighboring tissue, the heparin containing adhesion-preventive barrier material of claim 16.

* * * * *